United States Patent [19]
Arzeno et al.

[11] Patent Number: 5,948,939
[45] Date of Patent: Sep. 7, 1999

[54] SELECTIVE AMIDINATION OF DIAMINES

[75] Inventors: Humberto B. Arzeno, Cupertino; David J. Morgans, Jr., Sunnyvale, both of Calif.

[73] Assignee: Syntex (U.S.A.) Inc., Palo Alto, Calif.

[21] Appl. No.: 07/870,841

[22] Filed: Apr. 20, 1992

Related U.S. Application Data

[63] Continuation of application No. 07/094,220, Sep. 8, 1987, which is a continuation-in-part of application No. 06/905,827, Sep. 10, 1986, abandoned, which is a continuation-in-part of application No. 06/905,828, Sep. 10, 1986, abandoned.

[51] Int. Cl.$^6$ ...................... C07C 279/14; C07C 229/26; C07C 229/18
[52] U.S. Cl. ........................ 562/439; 562/562; 562/104; 562/43
[58] Field of Search ............................ 546/147; 562/439, 562/562, 104, 43

[56] References Cited

U.S. PATENT DOCUMENTS

| | | | |
|---|---|---|---|
| 4,211,867 | 7/1980 | Rasmussen | 544/60 |
| 4,477,429 | 10/1984 | Silbering et al. | 424/52 |
| 4,656,219 | 4/1987 | Maryanoff et al. | 548/351 |
| 4,656,270 | 4/1987 | Maryanoff et al. | 544/148 |
| 4,762,821 | 8/1988 | Nester | 514/19 |

FOREIGN PATENT DOCUMENTS

| | | |
|---|---|---|
| 0012401 | 6/1980 | European Pat. Off. . |
| 0050800 | 5/1982 | European Pat. Off. . |
| 0137742 | 4/1985 | European Pat. Off. . |
| 0196841 | 10/1986 | European Pat. Off. . |
| 1587258 | 4/1981 | United Kingdom . |

OTHER PUBLICATIONS

U.S. Patent Application Serial No. 06/905,828, Filed Sep. 10, 1986, (Nestor).
J.J. Nestor, Jr. et al. "Pephtides–Structure and Funchtin", *Proc Eighth Amer. Peptide Symposium,* V.J. Hruby et al., Eds., Pierce Chem. Co., Rockford, IL, 1984, pp. 861–864.
W. Walter, *Angew. Chem.,* 67, 1955, pp. 275–276.
C.A. Maryanoff et al., *J. Org. Chem.,* 51, 1986, pp. 1882–1884.
J. March, "Advanced Organic Chemistry", 3rd Edition, Wiley–Interscience, New York NY, 1985, p. 244.
H. Bredereck et al., *Chem. Ber.,* 94, 1961, pp. 2278–2295.

*Primary Examiner*—Alan L. Rotman
*Attorney, Agent, or Firm*—Heller Ehrman White & McAuliffe

[57] ABSTRACT

An ω-guanidino-α-amino-acid (or its functional derivative) or a compound containing it may be prepared by the reaction of the ω-amino group of an α,ω-diamino acid (or its functional derivative) or a compound containing it with a formamidinesulfonic acid.

9 Claims, No Drawings

SELECTIVE AMIDINATION OF DIAMINES

CROSS-REFERENCE TO RELATED APPLICATIONS

This application is a continuation of our U.S. patent application Ser. No. 07/094,220, filed Sep. 8, 1987; which is a continuation-in-part of our Ser. No. 06/905,827 filed Sep. 10, 1986, now abandoned; and a C-I-P of Ser. No. 06/905, 828, filed Sep. 10, 1986, now abandoned.

BACKGROUND OF THE INVENTION

1. Field of the Invention

This invention relates to the selective amidination of diamines, and especially to ω-guanidino-α-amino acids, and to the preparation of these acids, their functional derivatives, and compounds, such as peptides, containing them.

2. Background to the Invention

Published European Patent Application No. 196,841 describes a number of $N^G,N^{G'}$-dialkylguanidino dipeptides, which are stated to be useful as angiotensin-converting enzyme (ACE) inhibitors. These dipeptides may be considered to contain the modified amino acids $N^G,N^{G'}$-dialkylarginine, $N^G,N^{G'}$-dialkylhomoarginine, and $N^G,N^{G'}$-dialkyldihomoarginine; and may be prepared by a number of methods, which include (1) the reductive condensation of one of these amino acids with an α-ketoamide to form the dipeptide, and (2) the alkylation of a precursor dipeptide containing an ω-amine group, e.g. a dipeptide based on ornithine, lysine, or homolysine, with an alkylating formamidine derivative (an amidinating agent). Both of these synthetic methods involve the amidination of an ω-amine group with an alkylating formamidine derivative such as a haloformamidine or an (alkylthio)formamidine (an S-alkylisothiourea): in (1) in the preparation of a starting material, and in (2) in the reaction itself, and are discussed in the above-mentioned application, as are the syntheses of the starting materials.

A synthesis of ethyl $N^G,N^{G'}$-diethyl-L-homoarginate hydrochloride is disclosed in J. J. Nestor, Jr., et al., "Peptides—Structure and Function", *Proc. Eighth Amer. Peptide Symposium*, V. J. Hruby and D. H. Rich, Eds., Pierce Chem. Co., Rockford Ill., 1984, pp. 861–4. However, the use of an S-alkylisothiourea as an alkylating agent is attended with two disadvantages: first, the yield of the desired ω-guanidino acid is low; and second, the byproduct of the reaction is a noxious alkyl mercaptan. If an S-methylisothiourea is chosen, as is commonly done, methyl mercaptan (a gas detectable at a concentration of 1 ppb), results.

W. Walter, *Angew. Chem.*, 67, 1955, p. 275, describes the reaction of formamidinesulfinic acid with glycine under basic conditions to yield 36% of N-(aminoiminomethyl) glycine, an α-guanidino acid. British Patent No. 1,587,258 (Aktieselskabet Gea) describes the preparation of guanidines by the reaction of ammmonia and primary amines with formamidinesulfonic acids, which may be mono- or di-substituted with alkyl or phenylalkyl groups. C. A. Maryanoff et al., *J. Org. Chem.*, 51, 1986, pp. 1882–4, describe the reaction of mono(alkyl or aryl) formamidinesulfonic acids with primary and secondary amines to prepare guanidines. U.S. Pat. No. 4,656,270 (Maryanoff et al.) describes a process for the preparation of certain guanidines, which process includes the preparation of an N-arylformamidinesulfonic acid by the oxidation of the corresponding N-arylthiourea with hydrogen peroxide in the presence of a molybdenum catalyst. U.S. Pat. No. 4,656,291 (Maryanoff et al.) describes a process for the preparation of certain guanidines, which process includes the preparation of a formamidinesulfonic acid by the oxidation of a thiourea with hydrogen peroxide in the presence of a molybdenum catalyst.

The disclosures of these, and all other documents cited in the specification of this application, are incorporated herein by reference.

SUMMARY OF THE INVENTION

This invention relates to the selective amidination of diamines, in particular to a method for preparing an ω-guanidino-α-amino acid or its functional derivative, or a compound, such as a peptide, containing it, by the reaction of an α,ω-diamino acid or its functional derivative, or a compound containing it, with a formamidinesulfonic acid.

The method may be represented schematically:

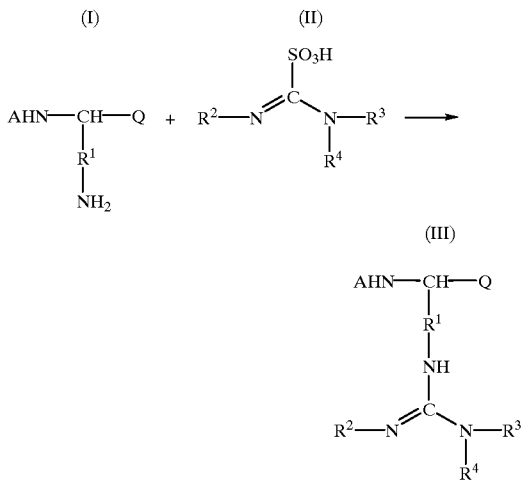

in which

A is H, R (wherein R is optionally substituted lower alkyl, phenyl, or aralkyl), R—O—CO—, peptidyl residue, or (peptidyl residue)-CO-(lower alkyl)-;

Q is a carboxylate-related group;

$R^1$ is optionally substituted lower alkylene; and $R^2$, $R^3$, and $R^4$ are each selected from H and R (wherein R is optionally substituted lower alkyl, phenyl, or aralkyl), with the proviso that at least one of $R^2$, $R^3$, and $R^4$ is not hydrogen.

Peptides that contain an ω-guanidino-α-amino acid or its functional derivatives may be prepared by a number of methods, which include (1) the coupling of an ω-guanidino-α-amino acid or its functional derivative with an amino acid or a functional derivative thereof to form the peptide, and (2) the alkylation of a precursor peptide containing an ω-amino group, e.g. a peptide based on an α,ω-diamino acid such as ornithine, lysine, or homolysine, with an alkylating formamidinesulfonic acid derivative (an amidinating agent).

Both of these synthetic methods involve the amidination of an ω-amino group with an alkylating formamidinesulfonic acid derivative: (1) in the preparation of a starting material for the synthesis of guanidino peptides, and (2) in the preparation of guanidino peptides. These two methods are discused in more detail in the "Compounds of Formula III" section of this disclosure.

DETAILED DESCRIPTION OF THE INVENTION

Definitions

As used in the specification and appended claims, unless specified to the contrary, the following terms have the meaning indicated:

"Lower alkyl" means a branched or unbranched saturated hydrocarbon chain containing from one to six carbon atoms, such as methyl, ethyl, isopropyl, n-hexyl, and the like.

"Lower alkoxy" means the group —OR, where R is lower alkyl as defined above, such as methoxy, ethoxy, isopropoxy, n-hexyloxy, and the like.

"Lower alkylene" means an unbranched saturated hydrocarbon chain containing from two to six carbon atoms, such as ethylene, 1,3-propylene, 1,5-pentylene, and the like.

"Aralkyl" means a ω-phenyl-substituted lower alkyl of one to three carbon atoms, such as benzyl, 2-phenylethyl, and the like.

"Optional" or "optionally" means that the subsequently described event or circumstance may or may not occur, and that the description includes instances where the event or circumstance occurs and where it does not.

"Optionally substituted", when applied to a compound or part thereof, means that one or more of the hydrogen atoms may be substituted by lower alkyl or lower alkoxy, both having one to three carbon atoms, halogen, or trifluoromethyl. Thus, "optionally substituted lower alkyl, phenyl, or aralkyl" includes methyl, 2-ethoxyethyl, phenyl, 4-ethylphenyl, 2-phenylethyl, 4-methoxybenzyl, and the like.

"Amino acid" includes both natural and non-natural amino acids and derivatives thereof. Preferred natural amino acids include the aliphatic amino acids such as alanine and leucine, hydroxyamino acids such as serine and threonine, dicarboxylic amino acids and their amides such as aspartic acid and glutamine, amino acids having basic functions such as hydroxylysine, lysine, arginine and histidine, aromatic amino acids such as phenylalanine, tyrosine and tryptophan, sulfur-containing amino acids such as cysteine and methionine, imino acids such as proline and hydroxyproline, and the like. Preferred non-natural amino acids include the cyclic imino acids analogs of proline such as 1,2,3,4-tetrahydroisoquinoline-3-carboxylic acid, 2,3-dihydroindole-2-carboxylic acid, 4,5-trimethyleneproline (2-azabicyclo[3.3.0]octane-3-carboxylic acid), and the like. "Amino acid" includes individual isomeric forms of chiral amino acids and racemic or non-racemic mixtures of these isomeric forms.

"Peptidyl residue" means an amino acid or peptide which is bonded to a —CO— or —NH— group (not part of the peptidyl residue) by an amide (peptide) bond.

"Carboxylate-related group" refers to a carboxylic acid group (—COOH), a carboxylate ion (—COO⁻) or salt thereof, an amide (as, e.g., in a peptide), ester, nitrile, acid halide, or the like, in particular to the optionally substituted amide, ester, or nitrile (i.e. where —Q of compound (I) is —CONR$^{11}$R$^{12}$, —COOR$^{13}$, or —C≡N, in which each of R$^{11}$ and R$^{12}$ is selected from H and R (R being optionally substituted lower alkyl, phenyl, and aralkyl), and R$^{13}$ is R).

"Functional derivative", when applied to α,ω-diamino acids, refers to replacement of the carboxylic acid group by another "carboxylate-related group". "Functional derivative" includes the case where the carboxylic acid group of the α,ω-diamino acid forms a peptide bond with the α-amine group of another amino acid or peptide, i.e. where the hydroxy portion of the carboxylic acid group is replaced by a peptidyl residue. "Functional derivative" also refers to replacement of one of the hydrogens of the α-amine group to form an amide (e.g. a peptide) or amine bond to the nitrogen, e.g. where A of compound (I) is R, R—O—CO—, a peptidyl residue, or (peptidyl residue)-CO-(lower alkyl)-. Preferred configurations of the (peptidyl residue)-CO-(lower alkyl)- group have the formula;

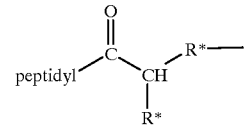

wherein R* is an alkyl group of one to five carbon atoms. "Functional derivative" further refers to a derivative of the amino acid wherein both the —COOH and H$_2$N— groups are functionalized as immediately previously described.

"Water-miscible organic solvent" includes (lower alkyl) alcohols (e.g. methanol and the like), ethers (e.g. tetrahydrofuran, dioxane, dimethoxyethane, and the like), and the like.

"Polar organic solvent" includes solvents such as acetonitrile and the like.

"Pharmaceutically acceptable salts" of a compound means those salts which retain the biological effectiveness and properties of the compound and which are not biologically or otherwise undesirable. "Pharmaceutically acceptable salts" includes acid addition salts of compounds containing basic groups, e.g. amines, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like. "Pharmaceutically acceptable salts" also includes salts of compounds containing carboxylate groups formed with inorganic bases such as sodium hydroxide, potassium hydroxide, calcium hydroxide, aluminum trihydroxide, magnesium hydroxide or with organic bases such as isopropylamine, N-methylglucamine, glucamine, trimethylamine, diethylamine, ethanolamine, 2-dimethylaminoethanol or tromethamine.

Compounds of Formula I

The diamino acids of compound (I) of this invention are generally commercially available, or may readily be prepared by methods known to those of ordinary skill in the art. Preferred diamino acids are those where the alkylene group contains from three to five carbon atoms, i.e. ornithine, lysine, and homolysine; and a particularly preferred diamino acid is lysine. The diamino acids are asymmetric, and may be available as (R)-, (S)-, and (R,S)-acids. The preparation of this invention is equally applicable to each form, and does not cause racemization at the α-carbon.

Functional derivatives of the diamino acids constituting compound (I) of this invention may be readily prepared from the diamino acids by methods known to those of ordinary skill in the art, e.g. esterification of the carboxylate group with alcohols, protection of the α-amine group with t-butoxycarbonyl, etc.; and a number of functional derivatives, such as esters and Nα-protected compounds, are commercially available, e.g. from Sigma Chemical Company or other biochemical suppliers. Preferred functional derivatives of the diamino acids constituting compound (I)

of this invention, other than peptides, are the esters of the acids, especially the lower alkyl esters, and the Nα-protected derivatives of the acids and esters, such as the Nα-t-butoxycarbonyl acids and esters.

Peptides containing the diamino acids constituting compound (I) of this invention may be prepared by methods of peptide synthesis known to those of ordinary skill in the art; and a number of peptides are commercially available. Preferred peptides are (S)-2-[(S)-N-[(S)-1-carboxy-5-aminopentyl]alanyl]-1,2,3,4-tetrahydro-isoquinoline-3-carboxylic acid and its esters, and the similar dipeptides disclosed as precursors to the $N^G,N^{G'}$-dialkylguanidino dipeptides in Published European Patent Application No. 196,841 referred to previously.

Compounds of Formula II

Compounds of formula II may be prepared by the method of C. A. Maryanoff et al., *J. Org. Chem.*, 51, 1986, pp. 1882–4, for sulfonic acids from thioureas (or by the references cited therein for that purpose), by the methods of U.S. Pat. Nos. 4,656,270 and 4,656,291, or by the following modification of that procedure. The starting thioureas are generally commercially available, or may readily be prepared by methods known to those of ordinary skill in the art. Preferred thioureas are those of the formula $R^2HN-C(S)-NR^3R^4$ where each of $R^2$ and $R^3$ is R, and $R^4$ is H; more preferred of those are where each of $R^2$ and $R^3$ is optionally substituted lower alkyl, and $R^4$ is H; and particularly preferred is 1,3-diethyl-2-thiourea. Other preferred thioureas are those where $R^2$ is optionally substituted phenyl and each of $R^3$ and $R^4$ is hydrogen, e.g. 1-phenyl-2-thiourea. The thiourea and an alkali molybdate (0.001–0.1 equivalents, with 0.002–0.01 equivalents being preferred) are dissolved or suspended in water, optionally containing a water-miscible organic solvent, and cooled to 0–15° C., preferably 0–50° C. The solution is stirred vigorously at that temperature, and approximately 3 equivalents of hydrogen peroxide are added dropwise sufficiently slowly to maintain the temperature below 20° C., preferably below 10° C. (typically, 30 minutes–4 hours, usually about 1–2 hours, is required). The solution is stirred for a further 30 minutes–4 hours, usually about 1–2 hours at that temperature, then allowed to warm to room temperature and stirred at room temperature for 10–30 hours. Excess oxidant is destroyed by cooling the solution to 0–20° C., preferably 0–10° C. (to minimize decomposition of the product), and adding a sufficient quantity of a reducing agent such as an alkali bisulfite until the solution becomes colorless or a test for peroxide is negative. The solution of the sulfonic acid may be filtered and used directly, or the acid may be isolated, if desired. If it is desired to isolate the acid, a relatively smaller amount of water may be used initially (e.g. 0.5 mL/mmol thiourea), and the acid may be isolated by methods such as removal of the solvent, e.g. by lyophilization of the solution, followed by dissolution of the solid acid in a lower alkyl alcohol (e.g. methanol) and precipitation with, e.g. diethyl ether; if it is desired to use the sulfonic acid directly, a relatively larger volume of water (e.g. 1.2 mL/mmol thiourea) is preferred.

Compounds of Formula III

The method of preparation of the desired compound of formula III is largely dependent upon the properties of the precursor compound of formula I, e.g. whether the compound of formula I is water-soluble. Since the reaction of compounds of formula I with formamidinesulfonic acid is relatively slow, conditions may be chosen to maximize the formation of the ω-guanidino derivative while minimizing formation of the α,ω-bis(guanidino) derivative. For example, the reaction may, but need not, be carried out in the presence of an auxiliary base soluble in the reaction solvent. If an auxiliary base is not used, it is preferred that the compound of formula I be present in excess over the formamidinesulfonic acid, as excess sulfonic acid would protonate the ω-amine group and render it less reactive. If an auxiliary base is used, an excess of the formamidinesulfonic acid may be employed to increase the rate of reaction; however, when the α-amine of the compound of formula I is unsubstituted, the excess should be small to avoid formation of the α,ω-bis(guanidino) derivative. Similarly, a wide range of reaction temperatures may be employed, from −10° C. to as high as reflux temperature of the solvent, typically between about 0° C. and room temperature, provided that these are otherwise consonant with the compound of formula I, e.g. they do not cause racemization at asymmetric carbon atoms, etc. The general reaction conditions described in the Maryanoff et al. article or patents previously referred to may be taken as a basis for suitable conditions, or the methods described in the following paragraphs and the Examples may be employed.

When the compound of formula I is water-soluble, e.g. when the compound of formula I is a diamino acid, a non-esterified peptide, or the like, the following method is suitable. The compound of formula I is dissolved in sufficient aqueous strong base (suitable strong bases include sodium hydroxide, potassium hydroxide, and the like) to give a solution of pH about 10–12, preferably 10.5–11. This solution is vigorously stirred, and maintained at that pH (e.g. by the addition of appropriate amounts of concentrated aqueous strong base) while the appropriate sulfonic acid is added, e.g. by addition of a solution prepared as above. The addition may take place over 1–72 hours, typically 6–24 hours. When the addition is completed, the reaction mixture is stirred for 5–25 hours, at a temperature about room temperature if the addition has taken place under cooling. The total reaction time, ratio of reactants, presence of base, etc., may be varied depending on the relative reaction rates at the α- and ω-nitrogen atoms, and one of ordinary skill in the art should be able to determine suitable parameters for the reaction without undue experimentation, having regard to his general knowledge in view of this disclosure. The product of formula III may then be isolated by conventional methods, as, e.g. by the methods disclosed in the Maryanoff et al. article or patents. Optionally, the free amino groups of the product of formula III may be protected by suitable amino-protecting agents, e.g. benzyloxycarbonyl, which is introduced by treating compounds of formula III with benzyl chloroformate in the presence of base, or t-butoxycarbonyl, which is introduced by treating compounds of formula III with di-t-butyl dicarbonate in the presence of base. In particular, the product may be carried in solution into another reaction, e.g. the ω-guanidino-α-amino acid may be protected, as by formation of the Nα-t-butoxycarbonyl derivative, and the resulting t-BOC guanidinoamino acid isolated.

If the compound of formula I is not sufficiently soluble in aqueous base (and it is generally desirable that the solution of compound I not be too dilute, as otherwise the reaction would be excessively slow), the aqueous base of the previous paragraph may be replaced by a solution of a base in a mixture of water and a water-miscible organic solvent, e.g. a water/methanol mixture.

If the compound of formula I is of low solubility in aqueous base, e.g. when the compound lacks ionizable amine or carboxylate groups, such as when the compound is a peptide diester, a polar organic solvent in which the sulfonic acid is also soluble may instead be used. A preferred solvent is acetonitrile, and preferred bases, when employed, are non-reactive organic bases at least as basic as triethylamine, e.g. tertiary amines such as triethylamine, N-methylpiperidine, and the like. The compound of formula I is dissolved in the solvent, and the sulfonic acid (as a solid or in solution) added with vigorous stirring. The reaction conditions are similar to those given above for aqueous solvents, and the comments above are applicable to non-aqueous solvents.

It is understood that the compounds of formula III may exist in a zwitterionic form, any carboxylic groups being dissociated (—COO⁻) and any of the imino group(s) or the =N—R² group being associated with a proton.

The product of formula III may be subject to further conventional chemical processes in the preparation of a final product, e.g., hydrolysis of ester groups to form acids, formation of salts with bases or acid addition salts, esterification of carboxylic acid groups, and the like, not affecting the guanidino moiety, and such optional additional chemical processes are to be considered within the scope of this invention when accompanying the amidination method of this invention previously described.

The procedures described above are particularly applicable to the preparation of ACE inhibitors of the formula (A)

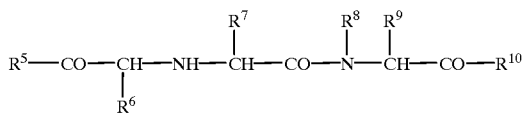

(A)

wherein $R^5$ represents hydroxy, lower alkoxy, benzyloxy or amino optionally substituted with one or two lower alkyl groups;

$R^6$ and $R^7$ represent (1) hydrogen or preferably lower alkyl (optionally omega-substituted with phenyl or naphthyl, less preferred omega-substituted with di(lower)alkylguanidino), or (2)

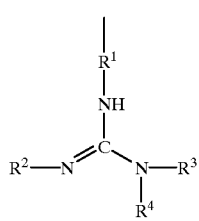

wherein $R^1$, $R^2$, $R^3$ and $R^4$ have the meanings set forth in the SUMMARY OF THE INVENTION;

one of $R^6$ and $R^7$ being (1), the other being (2); and the group

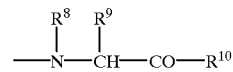

is an amino acid residue selected from the group of imino acid residues, preferably cyclic imino acid residues in which the subgroup

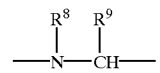

forms a heterocyclic radical containing one nitrogen atom and up to 9 ring carbon atoms, in particular said cyclic imino acid residue is or is derived from proline, hydroxyproline or proline analogs, and $R^{10}$ is hydroxy, lower alkoxy, benzyloxy or amino optionally substituted with one or two lower alkyl groups;

and their pharmaceutically acceptable salts, i.e. compounds of formula III in which either:

(a)

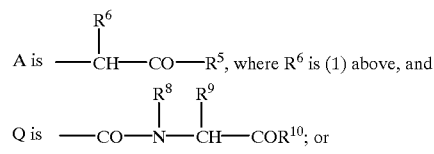

(b)

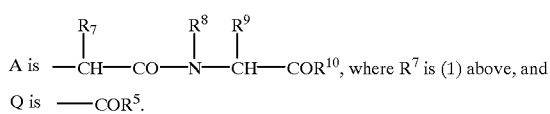

The process comprises alkylating a peptide of the formula (A*)

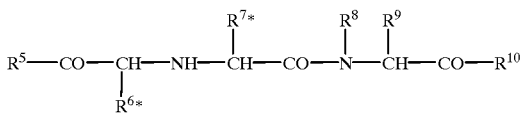

wherein one of $R^{6*}$ and $R^{7*}$ is —(CH₂)ₙNH₂ and the other of $R^{6*}$ and $R^{7*}$ is (1), preferably the compound (S)-2-[(S)-N-[(S)-1-carboxy-5-aminopentyl]-alanyl]-1,2,3,4-tetrahydro-isoquinoline-3-carboxylic acid and its esters, with an alkylating agent of the formula

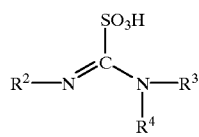

wherein $R^2$, $R^3$ and $R^4$ are as previously defined.

Precursors of formula A* are either known from the literature, can be made by known methods from known starting materials (e.g. Published European Patent Application Nos. 12401, 65301 and 79022) or can be prepared according to the "Compounds of Formula I" section of this disclosure.

The peptide of formula A* is alkylated according to the method of the present invention with a formamidinesulfonic acid derivative. The reaction is carried out according to the general reaction conditions described above.

The peptides of formula A or their precursors can also be produced using the known solid-phase technique, in particular using as solid phase polyamide resins that are swellable by polar solvents such as water. After completion of the synthesis the peptide may be removed from the polyamide by hydrolysis, hydrogenolysis, or transesterification.

The ω-guanidino-α-amino acids prepared may be used to form peptides including the ACE inhibitors of formula A by conventional methods for peptide synthesis including the process described in Published European Patent Application No. 196,841.

The compounds of formula A are ACE inhibitors and thus block the conversion of the decapeptide angiotensin I to angiotensin II, a highly potent pressor substance. Thus, ACE inhibitors can lower blood pressure by inhibiting the biosynthesis of angiotensin II, especially in animals and humans whose hypertension is angiotensin II related. Furthermore, ACE degrades the vasodilating substance bradykinin. Therefore, ACE inhibitors may lower blood pressure by potentiating bradykinin's effects, as well as by inhibiting angiotensin II. Although the relative importance of these and other possible mechanisms remains to be established, ACE inhibitors are known to be effective antihypertensive agents in a variety of animal models and are useful clinically, for example, in many human patients with malignant renovascular and essential hypertension.

EXAMPLES

The following Examples are provided for illustration of this invention and the best mode of practicing it, and should not be construed to limit it.

Example 1

Preparation of N,N'-diethylformamidinesulfonic acid.

A. 1,3-diethyl-2-thiourea (85 g, 643 mmol) and sodium molybdate dihydrate (415 mg, 1.7 mmol) were dissolved in water (850 mL), and the resulting solution cooled to 0–50° C. Hydrogen peroxide (15%, 410 mL, 1808 mmol) was added dropwise to the solution with stirring over 3 hours, while keeping the temperature below 10° C. After the addition was complete, the solution was stirred at that temperature for one hour, then allowed to warm to room temperature with stirring, and stirred at room temperature for 20 hours. The reaction mixture was then cooled below 10° C. and the excess oxidant was destroyed by the addition of solid sodium bisulfite (the addition being ended when the original yellowish color of the solution disappeared). The solution of N,N'-diethylformamidinesulfonic acid was then filtered and used without further treatment in the preparation of a guanidinoamino acid (see Example 2 below). Alternatively, the solution was lyophilized to remove water, and the lyophilized product dissolved in methanol and precipitated with diethyl ether to provide the solid N,N'-diethylformamidinesulfonic acid.

B. Substituting for 1,3-diethyl-2-thiourea, in the procedure of Part A of this Example,
1,3-dimethyl-2-thiourea, or
1,3-di-n-propyl-2-thiourea, one obtains, respectively,
N,N'-dimethylformamidinesulfonic acid, or
N,N'-di-n-propylformamidinesulfonic acid.

C. Similarly, substituting 1-phenyl-2-thiourea for 1,3-diethyl-2-thiourea, and using a similar procedure to that of Part A of this Example (replacing water as a solvent with methanol/water), there was obtained N-phenylformamidinesulfonic acid.

Example 2

Preparation of Nα-t-butoxycarbonyl-$N^G,N^{G'}$-diethyl-(R)-homoarginine (BOC-Deh).

A. To (R)-lysine hydrochloride (104 g, 569 mmol) was added sufficient 10% aqueous sodium hydroxide to give a solution of pH 10.65. The solution was cooled in an ice bath, and the solution of N,N'-diethylformamidine-sulfonic acid prepared in Part A of Example 1 added dropwise, with vigorous stirring, over 2 hours. During the addition, the pH was maintained at 10.65±0.05 by the addition of concentrated (20%) aqueous sodium hydroxide solution. After the addition was complete, the solution was allowed to warm to room temperature with stirring, and stirred at room temperature overnight. At this point, $N^G,N^{G'}$-diethyl-(R)-homoarginine may be isolated from the solution if desired. However, since the acid is conventionally used synthetically as the Nα-t-BOC derivative, it was convenient to derivatize it without isolation.

The reaction mixture was cooled to 0° C., dioxane (1 L) added, and di-t-butyl dicarbonate (200 g, 915 mmol) in dioxane (200 mL) added dropwise, with stirring. The mixture was stirred at room temperature for three hours, maintaining the pH at 10.0±0.3 by the addition of 10% aqueous sodium hydroxide solution. The solution was then filtered, and the filter cake washed with methanol The washings were combined with the filtrate, and the resulting solution reduced to half its volume. The solution was then extracted with ethyl acetate (2×100 mL), acidified to pH 6.4 with 10% aqueous hydrochloric acid, and again extracted with ethyl acetate (2×100 mL). The resulting aqueous solution was then evaporated to dryness, and the residue dissolved in a minimum quantity of ethanol at 50° C. and filtered. Silica gel (600 g) was added to the solution, which was then evaporated to dryness. The solid was added to a 2 Kg silica gel column packed in acetonitrile, and eluted with acetonitrile (2 L), acetonitrile/water 95:5 (8 L), acetonitrile/water 90:10 (8 L), acetonitrile/water 85:15 (8 L), and acetonitrile/water 80:20 (16 L). The fractions containing pure BOC-Deh (examined by tlc on silica gel, eluted with acetonitrile/water 80:20) were combined, evaporated to dryness, redissolved in warm ethanol, filtered, evaporated, triturated with ether, and dried under vacuum. 160 g of pure BOC-Deh was obtained.

B. Similarly, following the procedure of Part A of this Example and substituting (S)-ornithine hydrochloride for (R)-lysine hydrochloride, there was obtained Nα-t-butoxycarbonyl-$N^G,N^{G'}$-diethyl-(S)-arginine.

C. Similarly, following the procedure of Part A of this Example and substituting a solution of N-phenyl-formamidinesulfonic acid for the solution of N,N'-diethyl-formamidinesulfonic acid, there was obtained Nα-t-butoxycarbonyl-$N^G$-phenyl-(R)-homoarginine.

Example 3

Preparation of (S)-2-[(S)-N-[(S)-1-carboxy-5-$N^G,N^{G'}$-diethylguanidinopentyl]alanyl]-1,2,3,4-tetrahydroisoquinoline-3-carboxylic acid.

A. An aqueous solution containing 11.4 mmol of (S)-2-[(S)-N-[(S)-1-carboxy-5-aminopentyl]alanyl]-1,2,3,4-tetrahydroisoquinoline-3-carboxylic acid (prepared by the methods described in Published European Patent Application No. 196,841, referred to previously) was adjusted to pH 10.3 by the addition of solid sodium hydroxide. N,N'-Diethylformamidinesulfonic acid (1 g, 5.5 mmol) was added in one portion, with stirring, and the pH adjusted to 10.7 with 20% aqueous sodium hydroxide solution. Additional N,N'- diethylformamidinesulfonic acid (4.6 g, 25.5 mmol) was added in small portions over the next 30 hours, and 20% aqueous sodium hydroxide added as needed to maintain pH 10.6–10.9. When the starting dipeptide had been fully consumed (as shown by tlc), the reaction mixture was acidified to pH 4.5 with glacial acetic acid; and the resulting solution applied to a reverse phase preparative HPLC column of Lichoprep C18 and eluted with acetonitrile/aqueous ammonium acetate (0.05 M, pH 4.5) to effect purification. The purified guanidinodipeptide was isolated from the appropriate column fractions (tested by tlc or hplc) by standard techniques well-known to those of ordinary skill in the art. A salt of the title compound or an acid addition salt of the title compound are prepared by conventional methods.

B. N,N'-diethylformamidinesulfonic acid (4.94 g, 27.4 mmol) was added in one portion to a solution of benzyl (S)-2-[(S)-N-[(S)-1-methoxycarbonyl-5-aminopentyl]-alanyl]-1,2,3,4-tetrahydroisoquinoline-3-carboxylate (14.65 g, 30.5 mmol) (prepared by the methods described in Published European Patent Application No. 196,841, referred to previously) in acetonitrile (115 mL), with stirring at room temperature. After stirring at room temperature overnight, the reaction mixture was applied to a silica gel column, and eluted with acetonitrile/acetic acid/water mixtures to effect purification. Purified benzyl (S)-2-[(S)-N-[(S)-1-methoxycarbonyl-5-$N^G,N^{G'}$-diethylguanidinopentyl]-alanyl]-1,2,3,4-tetrahydroisoquinoline-3-carboxylate was isolated from the appropriate column fractions (tested by tlc) by standard techniques well-known to those of ordinary skill in the art. The free title compound, a salt of the title compound, or an acid addition salt of the title compound are prepared by conventional methods.

We claim:

1. A method for the selective amidination of a diamino compound of formula I:

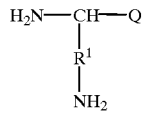
(I)

in which

Q is a carboxylate-related group; and $R^1$ is optionally substituted lower alkylene, to an α-amino-ω-guanidino compound of formula II:

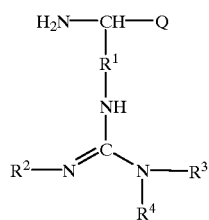
(II)

in which

Q is as previously defined; and $R^2$, $R^3$, and $R^4$ are each independently H or R (wherein R is optionally substituted lower alkyl, phenyl, or aralkyl), with the proviso that at least one of $R^2$, $R^3$, and $R^4$ is not hydrogen, which method comprises reactively contacting the diamino compound of formula I with a formamidinesulfonic acid of formula III:

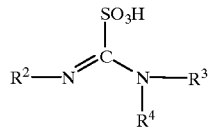
(III)

in which $R^2$, $R^3$, and $R^4$ are as previously defined under conditions favoring such selective amidination.

2. The method of claim 1 wherein Q is —COOH or —COOR (wherein R is defined as in claim 1).

3. The method of claim 2 wherein $R^1$ is —$(CH_2)_n$— and n is an integer of 3 to 5.

4. The method of claim 3 wherein $R^2$ and $R^3$ are each independently optionally substituted lower alkyl and $R^4$ is hydrogen.

5. The method of claim 4 wherein $R^2$ and $R^3$ are each ethyl.

6. The method of claim 3 wherein $R^2$ is optionally substituted phenyl and $R^3$ and $R^4$ are each hydrogen.

7. The method of claim 6 wherein $R^2$ is phenyl.

8. The method of claim 1 wherein the diamino compound of formula I is lysine.

9. The method of claim 8 where the formamidinesulfonic acid of formula II is N,N'-diethylformamidinesulfonic acid.

* * * * *